United States Patent
Baker et al.

(10) Patent No.: US 6,628,981 B2
(45) Date of Patent: Sep. 30, 2003

(54) ADAPTIVE HEART RATE PREDICTION ALGORITHM FOR COMPUTED TOMOGRAPHY IMAGING

(75) Inventors: Steven D. Baker, Morton, IL (US); DeAnn Marie Haas, Germantown, WI (US); Darin R. Okerlund, Muskego, WI (US); Sankar V. Srinivas, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 10/045,349

(22) Filed: Nov. 9, 2001

(65) Prior Publication Data

US 2003/0092983 A1 May 15, 2003

(51) Int. Cl.$^7$ .................................................. A61B 5/00
(52) U.S. Cl. ........................ 600/425; 600/428; 600/431; 600/509; 378/8; 378/95
(58) Field of Search ............................... 600/413, 428, 600/509, 521, 431, 425; 378/8, 95

(56) References Cited

U.S. PATENT DOCUMENTS

| | | | |
|---|---|---|---|
| 5,967,981 A | * 10/1999 | Watrous | 600/428 |
| 6,252,924 B1 | 6/2001 | Davantes et al. | |
| 6,256,368 B1 | 7/2001 | Hsieh et al. | |
| 6,266,553 B1 | * 7/2001 | Fluhrer et al. | 600/428 |
| 6,275,560 B1 | * 8/2001 | Blake et al. | 378/8 |
| 6,421,552 B1 | * 7/2002 | Hsieh | 600/425 |
| 6,470,208 B1 | * 10/2002 | Woodford et al. | 600/428 |
| 6,510,337 B1 | * 1/2003 | Heuscher et al. | 600/428 |

* cited by examiner

Primary Examiner—Ruth S. Smith
(74) Attorney, Agent, or Firm—George E. Haas; Quarles & Brady LLP

(57) ABSTRACT

A database is created that contains a plurality of data items gathered from many human beings wherein the data items affect the heart rate of a patient during a CT imaging procedure. Regression analysis is performed on the data in the database to derive an algorithm which defines an predicted heart rate value as a function of the plurality of data items. Specifically, values for the plurality of data items are obtained for the particular patient to be imaged and the algorithm is applied to those data items to predict the patient's heart rate which will occur during the CT imaging procedure. The predicted heart rate is employed to defined operating parameters of the CT procedure, such as the rate at which the x-ray source and detector rotate around a patient and the speed at which the patient moves through the imaging plane.

20 Claims, 1 Drawing Sheet

ADAPTIVE HEART RATE PREDICTION ALGORITHM FOR COMPUTED TOMOGRAPHY IMAGING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to computed tomography (CT) imaging, and more particularly, to cardiac CT imaging.

In one type of a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of attenuation of the x-ray beam. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a two-dimensional scan, data is processed to construct an image that corresponds to a two dimensional slice taken through the object. The prevailing method for reconstructing an image from two-dimensional data is referred to in the art as the filtered backprojection technique. This process converts the attenuation measurements from a scan into integers called "CT numbers" or "Hounsfield units", which are used to control the brightness of a corresponding pixel on a cathode ray tube display.

It is desirable to minimize the amount of time required to generate each image slice to minimize motion related image degradation. To reduce the total scan time, a "helical" scan may be performed in which the patient is moved while the data for the prescribed number of slices is acquired. Such a process generates a single helix from one fan beam helical scan. The helix mapped out by the fan beam yields projection data from which images in each prescribed slice may be reconstructed.

An alternative "half scan" technique also has been developed in which x-ray attenuation data for each slice is acquired during approximately half a rotation of the gantry. The half scan technique requires half the time to acquire data for a slice image, as compared to a full rotation scan.

Computed tomography is frequently employed to image a patient's heart. However, because the gantry requires time (e.g. one-half second) to make a full rotation, the continuous movement of the heart and the blood blurs the resultant images. Even the faster half scan technique still suffers from motion artifacts.

U.S. Pat. No. 6,275,560 describes an improved technique in which the x-ray emission from the CT system is gated by sensing the cardiac cycle of the patient and keying image acquisition to intervals during the cardiac cycle when the heart is relatively still. This technique uses an electrocardiograph (EKG) which produces an electrical signal representing the patient's cardiac waveform. The QRS wave of that waveform is used to determine when diastole of the heart occurs and the x-ray emission is activated during diastole. To reduce motion artifacts further, the x-ray attenuation data for a first half of the views during scan are acquired during the diastole of one heart cycle and the x-ray attenuation data for the other half of the views are acquired during diastole of the next heart cycle. This technique, referred to the "Snap-Shot Burst," in effect halves the time that the data is acquired during each cardiac cycle and thus less motion of the heart occurs during each acquisition period.

However, the cardiac gating techniques require knowledge of the cardiac activity in order that movement of the gantry and the table on which the patient is positioned can be synchronized with the acquisition intervals. The speed of the gantry has to be set at the beginning of the scan so that the emitter and detector will be in the proper angular positions during diastole. The table also must move at a speed in which the helical scan data is accurately acquired. Cardiac patients often suffer from arrhythmias, other heart conditions and anxiety which cause their heart rate to change unpredictably, thereby making selection of the gantry and table speeds difficult for an operator to determine.

SUMMARY OF THE INVENTION

A medical imaging system acquires image data at a plurality of views around a patient in an imaging plane. A method for operating such an imaging system comprises maintaining a database that contains a plurality of data items from a number of human beings. Regression analysis is performed on the plurality of data items in the database to derive an algorithm which defines an predicted heart rate value as a function of the plurality of data items. The algorithm then may be employed prior to imaging to predict a patient's heart rate which is likely to occur during an imaging procedure.

To make that prediction, values for the plurality of data items are obtained for the patient. The algorithm is applied to the obtained data items to determine an predicted heart rate value for the patient. Operating parameters of the medical imaging system then are set in response to the predicted heart rate value for the patient.

In the preferred embodiment of the invention the data items relate to characteristics of the patient and the imaging system operation which affect the patient's heart rate during an imaging procedure. For example, the plurality of data items are selected from a group comprising heart rate prior to imaging, heart rate during a previous imaging procedure, delay period between injection of a bolus and the bolus reaching a patient's organ of interest, the type of the bolus, rate of injection of the bolus, length of time of the imaging procedure, the patient's gender, patient's weight, patient's age and patient's ethnic background.

BRIEF DESCRIPTION OF THE OF THE DRAWINGS

DETAILED DESCRIPTION OF THE INVENTION

Figure 1:
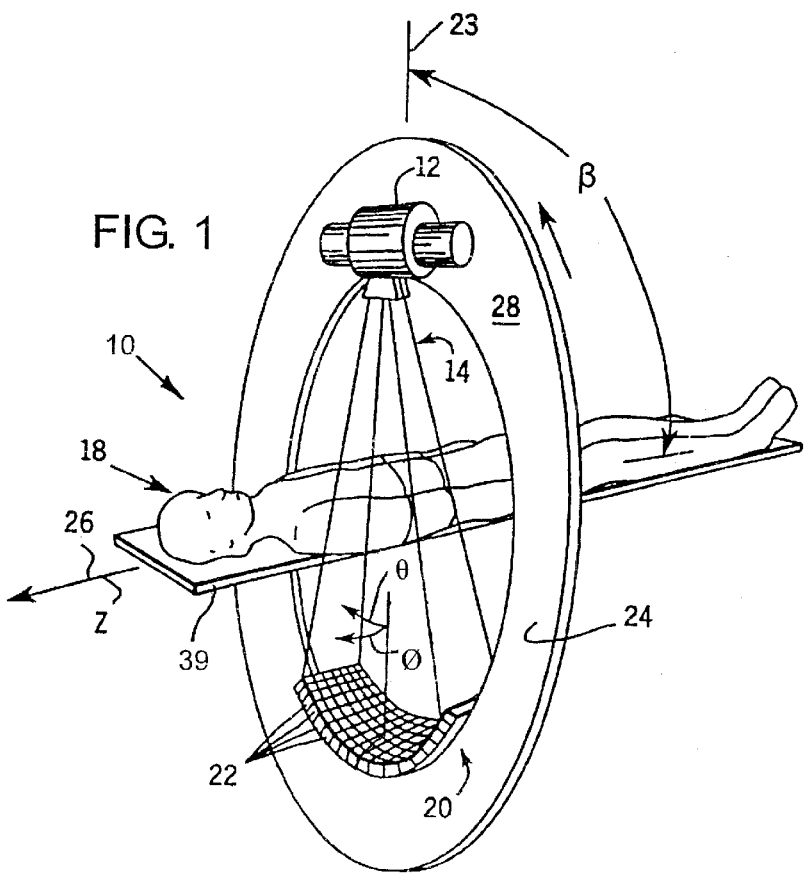
FIG. 1 is a schematic view of a gantry of a CT imaging system.

With initial reference to FIG. 1, a CT imaging system 10 includes an x-ray source 12 oriented to project a conical beam of x-rays 14 from a focal spot through a patient 18 to be received by a two-dimensional detector array 20. The x-ray source 12 and the two-dimensional detector array 20 are mounted on opposite sides of a gantry 24 that rotates about an axis 26 generally located within the patient 18. The axis of rotation 26 forms the z-axis of a Cartesian coordinate system having its origin centered within the cone beam 14. The plane defined by the x and y axes of this coordinate system thus defines a plane of rotation, specifically the gantry plane 28 of the gantry 24.

Rotation of the gantry 24 is measured by angle $\beta$ from an arbitrary reference position 23 within the gantry plane 28. Angle $\beta$ varies between 0 and $2\pi$ radians (360°). The x-rays of the cone beam 14 diverge from the gantry plane 28 by angle $\emptyset$ and diverge along the gantry plane 28 by angle $\theta$. The two-dimensional detector array 20 is arranged as a section of the surface of a sphere having a center at the focal spot of the source 12, and its array of detector elements 22 is arranged to receive and make intensity measurements along the rays of the cone beam 14 throughout the angles of $\emptyset$ and $\theta$ of the cone beam 14.

The two-dimensional detector array 20 includes a number of detector elements 22 arranged over the area of the detector array in generally perpendicular columns and rows to detect a projected image of the x-rays 14 passing through the patient 18. For example, detector array 20 may include sixteen rows disposed along the z axis with each row may having 1,000 separate detector elements. Gas or solid state detectors may be employed to produce an electrical signal proportional to the x-ray flux received over a sampling period.

Figure 2:
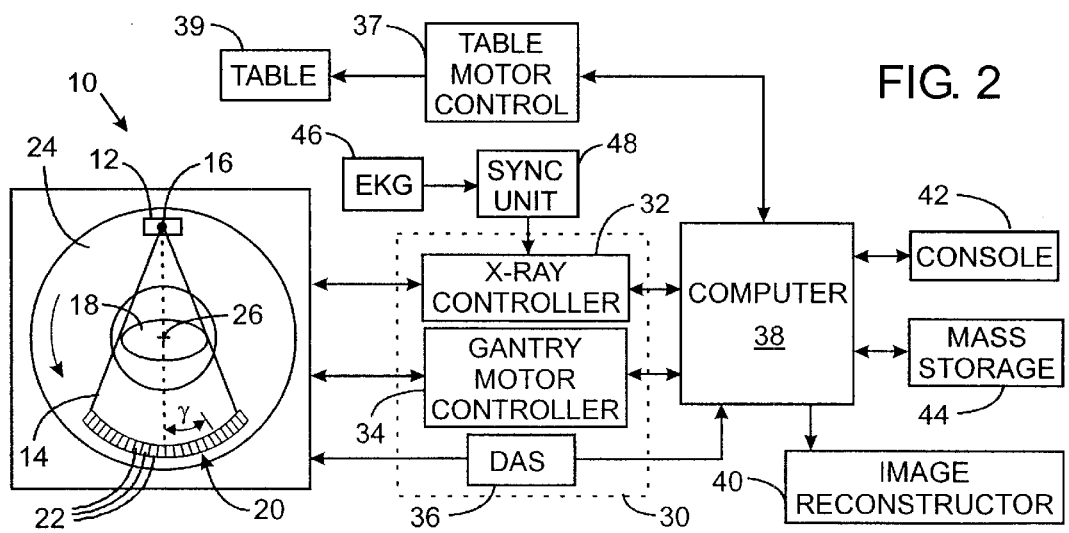
FIG. 2 is a block diagram of a CT imaging system in which the present invention may be employed.

Referring to FIG. 2, the control subsystem of the CT imaging system 10 has gantry associated control modules 30 which include: an x-ray controller 32, which provides power and timing signals to the x-ray source 12, and a gantry motor controller 34, which controls the rotational speed and position of the gantry 24. A data acquisition system (DAS) 36 receives projection data from the two-dimensional detector array 20 and converts the data into digital form for later computer processing, while preserving the values of $\emptyset$, $\theta$ and the gantry angle $\beta$ at which the data was taken. The x-ray controller 32, the gantry motor controller 34 and the data acquisition system 36 are connected to computer 38. The computer 38 also governs operation of a table motor control 37 which drives a motor that moves the patient table 39 along the z-axis 26.

The computer 38 is a general purpose minicomputer programmed to acquire and manipulate projection data which then is supplied to an image reconstructor 40 which performs high speed image reconstruction according to methods known in the art.

The computer 38 receives commands and scanning parameters via operator console 42, which has a display monitor and a keyboard. The monitor displays operational information related to the performance of the CT imaging system and displays the reconstructed image. The keyboard enables an operator to enter parameters for the CT scan as will be described. A mass storage device 44 provides a means for storing operating programs.

An electrocardiograph (EKG) 46 is utilized to sense the cardiac activity of the patient. Heart activity is characterized by two distinct periods called systole and diastole. During systole, the heart muscle is contracting the volume of the left ventricle to pump the contents out through the aortic valve. At the end of the systole, the left ventricle has its smallest volume since it has been contracted to pump blood out. During the diastole, or the diastolic period, the left ventricle is filling through the mitral valve. The end of the diastole is the point at which the left ventricle has its largest volume since it is filled with blood ready to be pumped out. For the duration of the diastolic period, the heart is relatively motion-free allowing images generated from data collected during this period to be clearer as a result of the limited movement.

The electrocardiograph 46 is of a conventional design which utilizes electrodes attached to the patient's chest to detect electrical activity of a heart. The electrical activity is represented by a standard cardiac waveform signal produced at an output of the electrocardiograph 46. A portion of the signal known as the QRS complex contains the R-wave, which is the most prominent, highest amplitude, feature of the entire signal, and the cardiac cycle is typically defined as beginning with an R-wave and continuing until the occurrence of the next R-wave.

That output signal from the electrocardiograph 46 is applied to a synchronization (SYNC) unit, or circuit, 48 which interfaces to the x-ray controller 32. The signal received from the synchronization unit 48 enables the x-ray controller 32 to synchronize production of short bursts of x-rays during a selected portion of a cardiac cycle of a patient. Specifically the cardiac waveform signal is used to determine the timing and duration of data collection. In one embodiment, the synchronization unit 48 activates x-ray emission after delaying a selected period of time from commencement of a cardiac cycle so that the x-ray beam 14 is emitted during the selected period of the cardiac cycle.

X-ray attenuation data collected from a series of these short bursts of x-rays then are utilized to generate an image of the heart by conventional backprojection methods. Image quality is improved and motion artifacts reduced by collecting x-ray attenuation data during a resting period of the heart.

Although the activation of the x-ray beam can be dynamically synchronized to each cardiac cycle which occurs during the scan, other parameters such as gantry speed, table speed, and slice thickness must be defined prior to the scan and cannot be changed during the scan. The correct combination of these parameters is important to yield images with minimal motion artifacts as their selection determines whether the x-ray source and detector will be properly located during diastolic period of each cardiac cycle. Hence, in order to consistently image the heart, an accurate prediction must be made of the patient's initial heart rate and the range of heart rate variation which will occur during the cardiac scan. Heretofore, these predictions and the scan parameters determined from them had to be derived manually by the system operator and often were approximations, the accuracy of which depended on the experience level of the operator.

The present algorithm predicts the initial heart rate and the heart rate range of the patient during the imaging scan by monitoring the heart rate variation during pre-scan conditions, and applying the cardiac observations to a database of cardiac activity observations from a large population of patients. Regression analysis performed on the information in that database yields a transfer function that relates a patient's characteristics to a heart rate which likely will occur during an imaging procedure. When a particular patient is to be examined, the requisite characteristics are observed and applied to the transfer function to produce a prediction of that patient's heart rate during the scan. Before the start of the actual imaging scan, the predicted heart rate is used to set the scan parameters (e.g. table speed, gantry speed and slice thickness).

The algorithm is adaptive as it learns to better predict the heart rate by employing the results from each cardiac scan. Initially a baseline algorithm is derived by the system manufacturer from regression analysis performed on data collected from patients at a number of prominent clinical and research sites. The regression analysis utilizes a number of clinical factors as dependent variables to produce the best possible baseline algorithm. The baseline algorithm is incorporated into the software of a CT imaging system delivered to medical facility site. Thereafter, each time a cardiac scan is performed by that particular CT imaging system, data regarding the patient's cardiac activity is added to the previously collected patient data and regression analysis is applied to the updated data. This allows the algorithm to re-optimize to the specific site factors each time a cardiac CT scan is conducted, thereby improving the quality of the heart rate prediction and the quality of the scan protocol selection. It should be understood that various medical facilities utilize slightly different scan procedures and thus, the system operation may be dependent on the particular site in which the CT imaging system is installed. For example, different sites utilize their own patient preparation and breathing protocols. In addition, heart behavior characteristic of patients may vary depending upon factors related to their native geographical location. Thus, there is a need to adapt the prediction algorithm to each specific CT imaging system.

Figure 3:
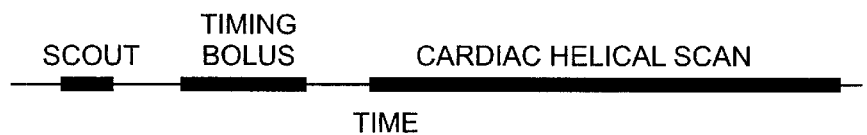
FIG. 3 is a time line showing the stages of a typical cardiac CT imaging procedure.

In order to understand some of the factors which are used to predict the heart rate, an understanding of the overall CT cardiac imaging procedure is necessary. The examination commences by the patient laying on the table 39 of the CT system and being connected to the electrocardiograph 46, which begins sensing the electrical activity of the heart and producing the cardiac wave form. This information is utilized to determine the heart rate of the patient prior to cardiac scan. With reference to FIG. 3, the CT system then is operated to produce a "scout" scan of the patient which is a preliminary scan of short duration to define the limits of table travel and other parameters to ensure that the heart will be imaged completely during the subsequent actual CT scan. During the scout scan, the patient's average heart rate is determined by the electrocardiograph 46 and stored in the memory of the CT system. In addition, the mean, standard deviation, minimum, maximum values for the heart rate and the number of heart beats which occur during each pre-scan period also can be derived and stored.

In order to be able to distinguish the blood vessels of the heart from the surrounding tissue, a bolus is injected intravenously into the patient. The bolus is a solution which provides contrast between the blood flowing through the heart and the heart tissue, thus enabling the blood vessels to be distinguished in the resultant image. The bolus requires a certain amount of time to be carried by the circulatory system from the injection site to the heart in sufficient quantity to provide the desired contrast. Therefore, prior to the actual image scan, a timing bolus scan is conducted to determine that travel time. It should understood that the bolus is quickly removed from the blood by other organs of the heart and thus must be re-injected each time an image is to be produced. Thus, during the timing bolus scan, the CT system is operated and the technician injects the bolus and then observes the CT images to identify the amount of time required for the bolus to reach the heart in sufficient quantity to produce a high contrast image. This time period is entered into the CT imaging system for use during the actual cardiac scan. The type of bolus and the rate of injection are additional factors that are used by the present heart rate prediction algorithm and also are entered into the CT system via the operator console 42.

Average heart rate data continues to be acquired prior to, during and after the timing bolus CT scan and recorded in the system storage 44.

Patient attributes, such as gender, weight, age and ethnic background, that affect the heart rate and the heart rate change also are entered into the CT imaging system.

After values for these parameters have been either determined by the CT system or entered by the operator, the computer 38 performs regression analysis on the data collected from this particular patient along with the baseline data and data from previous scans by the particular CT system. The regression analysis derives an predicted heart rate for the present patient according to the expression:

$$\text{Predicted Heart Rate} = c + a1(HR1) + a2(HR2) + a3(\Delta 1HR) + a4(HR3) + a5(HR4) + a6(\Delta 2HR) + a7(HR5)$$

where c is a constant, a1, a2, a3, a4, a5, a6, and a7 are weighting factors for the associated patient characteristics as determined by the regression analysis; HR1 is the average heart rate that occurs prior to the scout scan, HR2 is the average heart rate that occurs during the scout scan, $\Delta 1HR$ is the percent change between heart rates HR1 and HR2 (HR2/HR1). HR3 is the average heart rate that occurs between the scout scan and the timing bolus, HR4 is the average heart rate that occurs during the timing bolus, $\Delta 2HR$ is the percent change between heart rates HR3 and HR4 (HR4/HR3); and HR5 is the average heart rate that occurs after the timing bolus. This expression may be expanded with additional terms for patient attributes, such as gender, weight, age and ethnic background.

However, because the p-value for the coefficients a1, a2, a4, and a5 are >0.05 (5%) and hence are not significant in regression, the predicted heart rate expression may be reduced to:

$$\text{Predicted Heart Rate} = c + a3(\Delta 1HR) + a6(\Delta 2HR) + a7(HR5).$$

The resultant predicted heart rate then is employed to calculate the table speed, gantry speed and slice thickness which will produce optimal images for the patient. Specifically, the heart rate determines the speed at which the gantry should rotate in order that the x-ray source and detector will be properly located during diastolic period of each cardiac cycle. If the Snap-Shot Burst technique is to be utilized, the speed of the table movement also is a function of the heart rate as rays of the x-ray beam must pass through the same section of the heart and then impinge on a row of the detector array during multiple cardiac cycles in order to have attenuation data from which to reconstruct a slice image. Thus if the table moves too fast, proper image date will not be available to freeze the motion of the heart The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention.

Accordingly, the scope of the invention should be determined from the following claims and not limited by the above disclosure.

What is claimed is:

1. A method for operating a medical imaging system in which data are acquired from a plurality of views around a patient in an imaging plane, said method comprising:

maintaining a database containing a plurality of data items produced during imaging procedures conducted on a plurality of human beings;

performing regression analysis on the plurality of data items in the database to derive an algorithm which defines a predicted heart rate value as a function of the plurality of data items;

obtaining values for the plurality of data items for the patient;

applying the algorithm to plurality of data items for the patient to determine a predicted heart rate value for the patient; and controlling operation of the medical imaging system in response to the predicted heart rate value for the patient.

2. The method as recited in claim 1 wherein the plurality of data items is selected from a group consisting of heart rate prior to a scout scan, heart rate during a the scout scan, heart rate prior to a bolus timing scan and heart rate after the bolus timing scan.

3. The method as recited in claim 1 wherein the plurality of data items is selected from a group consisting of heart rate prior to imaging, heart rate during a previous imaging procedure, delay period between injection of a bolus and the bolus reaching a patient's organ of interest, the type of the bolus, rate of injection of the bolus, and length of time of the imaging procedure.

4. The method as recited in claim 3 wherein the plurality of data items further comprise at least one physiological characteristic of the patient.

5. The method as recited in claim 3 wherein the plurality of data items is selected from a group consisting of patient's gender, patient's weight, patient's age and patient's ethnic background.

6. The method as recited in claim 1 further comprising:

adding the values for the plurality of data items for the patient to the database; and thereafter performing regression analysis of the plurality of data items in the database to derive another algorithm for subsequent use in operating the medical imaging system.

7. The method as recited in claim 1 wherein the algorithm is defined by the expression:

$$\text{Predicted Heart Rate}=c+a1(HR1)+a2(HR2)+a3(\Delta 1HR)+a4(HR3)+a5(HR4)+a6(\Delta 2HR)+a7(HR5)$$

where c is a constant, a1, a2, a3, a4, a5, a6, and a7 are weighting factors for the associated patient characteristics as determined by the regression analysis, HR1 is the average heart rate that occurs prior to the a scout scan, HR2 is the average heart rate that occurs during the scout scan, $\Delta 1HR$ is the percent change between heart rates HR1 and HR2 (HR2/HR1), HR3 is the average heart rate that occurs between the scout scan and the a timing bolus, HR4 is the average heart rate that occurs during the timing bolus, $\Delta 2HR$ is the percent change between heart rates HR3 and HR4 (HR4/HR3), and HR5 is the average heart rate that occurs after the timing bolus.

8. The method as recited in claim 1 wherein the algorithm is defined by the expression:

$$\text{Predicted Heart Rate}=c+a3(\Delta 1HR)+a6(\Delta 2HR)+a7(HR5)$$

where c is a constant, a3, a6, and a7 are weighting factors for the associated patient characteristics as determined by the regression analysis, $\Delta 1HR$ is the percent change between the average heart rate that occurs prior to a scout scan and the average heart rate that occurs during the scout scan, $\Delta 2HR$ is the percent change between the average heart rate that occurs between the scout scan and a timing bolus and the average heart rate that occurs during the timing bolus, and HR5 is the average heart rate that occurs after the timing bolus.

9. A method for performing a cardiac scan with a computed tomography imaging system in which data is are acquired by rotating an x-ray source and detector around a patient in an imaging plane, said method comprising:

maintaining a database containing a plurality of data items for each of a plurality of human beings;

performing regression analysis on the plurality of data items in the database to derive an algorithm which defines a predicted heart rate value as a function of the plurality of data items;

obtaining values for the plurality of data items for the patient;

applying the algorithm to plurality of data items for the patient to determine a predicted heart rate value for the patient; and employing the predicted heart rate value for the patient to control a rate at which the x-ray source and detector rotate around a patient.

10. The method as recited in claim 9 further comprising employing the predicted heart rate value for the patient to control a rate at which the patient moves through the imaging plane.

11. The method as recited in claim 9 wherein each of the plurality of data items maintained in the database relates to heart activity of the plurality of human beings.

12. The method as recited in claim 9 wherein the plurality of data items is selected from a group consisting of heart rate prior to a scout scan, heart rate during the scout scan, heart rate prior to a bolus timing scan and heart rate after the bolus timing scan.

13. The method as recited in claim 9 wherein the plurality of data items is selected from a group consisting of heart rate prior to imaging, heart rate during a previous imaging procedure, delay period between injection of a bolus and the bolus reaching a patient's organ of interest, the type of the bolus, rate of injection of the bolus, and length of time of the imaging procedure.

14. The method as recited in claim 13 wherein the plurality of data items further comprise at least one physiological characteristic of the patient.

15. The method as recited in claim 13 wherein the plurality of data items is selected from a group consisting of patient's gender, patient's weight, patient's age and patient's ethnic, background.

16. The method as recited in claim 9 further comprising:

adding the values for the plurality of data items for the patient to the database; and thereafter performing regression analysis of the plurality of data items in the database to derive another algorithm for subsequent use in operating the medical imaging system.

17. The method as recited in claim 9 wherein the algorithm is defined by the expression:

Predicted Heart Rate=$c+a3(\Delta 1HR)+a6(\Delta 2HR)+a7(HR5)$ where c is a constant, a3, a6, and a7 are weighting factors for the associated patient characteristics as determined by the regression analysis, $\Delta 1HR$ is the percent change between the average heart rate that occurs prior to the a scout scan and the average heart rate that occurs during the scout scan, $\Delta 2HR$ is the percent change between the average heart rate that occurs between the scout scan and a timing bolus and the average heart rate that occurs during the timing bolus, and HR5 is the average heart rate that occurs after the timing bolus.

18. A method for performing a cardiac scan on a patient with a computed tomography imaging system, said method comprising:

forming a database which contains a plurality of data items related to characteristics of the patient and the imaging system operation which affect the heart rate of the patient during an imaging procedure;

performing regression analysis on the plurality of data items in the database to derive an algorithm which defines a predicted heart rate value as a function of the plurality of data items;

obtaining values for the plurality of data items for the patient;

applying the algorithm to plurality of data items for the patient to determine a predicted heart rate value for the patient;

employing the predicted heart rate value for the patient to control a rate at which the x-ray source and detector rotate around a patient;

adding the values for the plurality of data items for the patient to the database; and thereafter performing regression analysis of the plurality of data items in the database to derive another algorithm for subsequent use in operating the medical imaging system.

19. The method as recited in claim 18 wherein the plurality of data items is selected from a group consisting of heart rate prior to imaging, heart rate during a previous imaging procedure, delay period between injection of a bolus and the bolus reaching a patient's organ of interest, the type of the bolus, rate of injection of the bolus, length of time of the imaging procedure, patient's gender, patient's weight, patient's age, and patient's ethnic background.

20. The method as recited in claim 18 wherein the plurality of data items is selected from a group consisting of heart rate prior to a scout scan, heart rate during a the scout scan, heart rate prior to a bolus timing scan and heart rate after the bolus timing scan.

* * * * *